United States Patent [19]
Kexin

[11] Patent Number: 6,084,676
[45] Date of Patent: Jul. 4, 2000

[54] NON-CONTACT NON-INVASIVE MEASURING METHOD AND APPARATUS

[75] Inventor: Xu Kexin, Kyoto, Japan

[73] Assignees: Kyoto Dai-Ichi Kagaku Co., Ltd., Kyoto; Kurashiki Boseki Kabushiki Kaisha, Okayama, both of Japan

[21] Appl. No.: 09/181,635

[22] Filed: Oct. 29, 1998

[30] Foreign Application Priority Data

Nov. 21, 1997 [JP] Japan ..................................... 9-337913

[51] Int. Cl.$^7$ ........................... G01B 11/14; G01N 33/48; A61B 5/00
[52] U.S. Cl. .............................. 356/375; 356/39; 356/41; 128/633; 600/322
[58] Field of Search ................................... 356/375, 376, 356/39, 41; 128/633, 634, 637, 644, 666, 667; 600/322

[56] References Cited

U.S. PATENT DOCUMENTS

| 4,701,049 | 10/1987 | Beckmann et al. . | |
| 5,337,744 | 8/1994 | Branigan | 356/41 |
| 5,436,455 | 7/1995 | Rosenthal et al. . | |
| 5,572,313 | 11/1996 | Zheng et al. . | |
| 5,782,757 | 7/1998 | Diab et al. | 356/41 |
| 5,786,592 | 7/1998 | Hok | 356/41 |
| 5,805,287 | 9/1998 | Pettersen et al. | 356/375 |
| 5,825,666 | 10/1998 | Freifeld | 356/375 |

FOREIGN PATENT DOCUMENTS 0 795 293  9/1997  European Pat. Off. .
0 801 297  10/1997  European Pat. Off. .

OTHER PUBLICATIONS

Patent Abstracts of Japan, vol. 097, No. 003, Mar. 31, 1997 & JP 08 299310 (Toa Medical Electronics Co., Ken Ishihara), Nov. 19, 1996 & U.S. Patent No. 5,769,076 (Asano Kaoru et al), Jun. 23, 1998.

*Primary Examiner*—Frank G. Font
*Assistant Examiner*—Roy M. Punnoose
*Attorney, Agent, or Firm*—Arent Fox Kintner Plotkin & Kahn, PLLC

[57] ABSTRACT

The distance between an image indicating a measured portion and a measuring apparatus is previously registered, a measured object is arranged in a prescribed space in a non-contact state, the position of a probe is so adjusted that two-dimensional image sensing means senses the previously registered image of the measured portion, the position of the probe is so adjusted that the distance up to the measured portion by distance measuring means reaches the previously registered distance, and orientation determination means irradiates the measured portion with a light beam while changing the orientation for determining an orientation maximizing the quantity of light transmitted through the measured portion. Thereafter the physical quantity measuring apparatus irradiates the measured portion with measuring light and senses output light from the measured portion for obtaining a physical quantity.

11 Claims, 15 Drawing Sheets (A - a)

(A - b)

(B - a)

(B - b)

CURRENT POSITION

ADJUSTED POSITION

ADJUSTMENT OF MEASURED AREA (DISTANCE)
(Z-COORDINATE)

ADJUSTMENT OF
MEASURING ORIENTATION ($\theta$-COORDINATE)

MEASUREMENT OF PHYSICAL QUANTITY (e.g., CONCENTRATION)
UNDER DETERMINED CONDITIONS ($X_0$, $Y_0$, $Z_0$, AND $\theta_0$)

NON-CONTACT NON-INVASIVE MEASURING METHOD AND APPARATUS

BACKGROUND OF THE INVENTION

1. Field of the Invention

The present invention relates to a method of non-invasively measuring a physical quantity such as a component concentration in a living body, such as a blood-sugar level in a human body, in a non-contact state and an apparatus therefor.

2. Description of the Prior Art

In order to measure a physical quantity in a living body, a measuring apparatus must interact with the surface of the measured body in some form. Also, in case of making measurements through the principle of absorption of light, interaction such as the application of light to the living body is unavoidable. In a measuring method carried out by directly bringing a probe with a sensor into contact with the living body, such contact exerts remarkable influence on the measured object, and hence a measurement error is increased unless such influence is suppressed to a minimum. Specifically, when the measured object is a conscious living thing such as a human, he is not only physically but also mentally influenced by the measuring method. Furthermore, the influence varies with the difference between the equilibrium state of the human and the state of the probe. There is the apprehension that a process for adjusting the equilibrium to a new state causes a disturbance on the measurement of the physical quantity to influence the measured value depending on the difference between the states, whether the human himself is conscious or unconscious.

Settlement of measuring conditions such as the position and the orientation for measurements by bringing a probe into contact with a measured object is being studied. However, no such measuring conditions are settled in a non-contact state, and a method in a contact state cannot be applied to measurements in a non-contact state as such. If the measuring conditions are determined while bringing the measured object into contact with a probe or the like, conscious or physical influence resulting from the contact is exerted on the measured value. In order to avoid such influence, a method of determining measuring conditions in a non-contact state is necessary. Specifically, for example, in case of measuring the concentration of a minor component such as hemal glucose concentration, an obtained signal is extremely weak by nature and physical or mental influence disorders the measured value to deteriorate a signal-to-noise ratio and causes difficulty in extraction of the signal if the measurement is made in a contact state. Such influence resulting from the contact is considered as one of the factors hindering improvement in accuracy of non-invasive glucose measurement at present.

The method of minimizing a measurement error resulting from such physical or mental influence is adapted to arrange the measured object in a space not to be in contact with the probe for measurements by irradiating the measured object with light from a measuring apparatus.

It is known that measurement errors result from fluctuation of relative positional relations between the measured object and the measuring apparatus in the case of making measurements in a non-contact state, although physical or mental influence following contact can be eliminated in this case (refer to Japanese Patent Laying-Open Gazette No. 9-49794 (1997)). Therefore, no accurate measurement result can be obtained unless the measured portion (the position irradiated with measuring light), the measured area (the area of the surface of the measured object irradiated with the measuring light, i.e., the distance between the measuring apparatus and the surface of the measured object) and the measuring orientation (the direction of incidence of the measuring light upon the measured surface) are precisely determined.

SUMMARY OF THE INVENTION

The object of the present invention is to obtain reproducible measured data by arranging a measured object in a space in a state not in contact with a probe and determining a relative position thereof with respect to a measuring apparatus.

According to the present invention, it is preferable to make measurements in such an ordinary state that a measured object, for example a human body, is already at thermal equilibrium under the room temperature. To this end, the present invention is adapted to set a measured portion in a prescribed space of a measuring apparatus in a non-contact state for determining the orientation of applied light and relative positional relation between a probe and the measured object, and making measurements regularly on a constant position and in a constant orientation. Thus, it is possible to non-invasively measure the physical quantity of the measured object in a non-contact manner regularly under the same measuring conditions.

In a measuring method according to the present invention, the image indicating the measured portion on the measured object, the distance between the image and a sensing position, and the orientation of a physical quantity measuring apparatus with respect to the measured portion in measurement are previously registered for measurements by determining the position and the orientation of the physical quantity measuring apparatus through the following steps.

(A) arranging the measured object in a prescribed space in a non-contact state while arranging positioning means on the sensing position of a probe for the sensing of the previously registered image of the measured portion with the positioning means and adjusting the position of the probe so that the position of the sensed image coincides with the position ($X_0$, $Y_0$) of the registered image;

(B) arranging distance measuring means on the sensing position of the probe and adjusting the position of the probe so that the distance up to the measured portion coincides with the previously registered distance ($Z_0$);

(C) arranging orientation determination means on the sensing position of the probe and determining such a sensing position that the measured portion is in the previously registered orientation ($\theta_0$); and (D) thereafter arranging the physical quantity measuring apparatus on the sensing position of the probe, moving the same to the position determined by the orientation determination means, thereafter irradiating the measured portion with measuring light from the physical quantity measuring apparatus and sensing output light from the measured portion thereby obtaining a physical quantity, as shown in FIG. 1.

Assuming that a surface perpendicularly intersecting with a ring surface through the center of a ring-shaped probe shown in FIG. 2 is an X-Y plane and an axis perpendicularly intersecting with the X-Y plane through the center of the probe is a Z-axis, the intersection point between the central circle of the ring and the Z-axis is referred to as the sensing position in the present invention.

The previously registered distance ($Z_0$) up to the measured portion is preferably equal to the radius of the ring-shaped probe. In this case, the measured portion comes to the center of the ring forming the probe. Also, when the ring forming the probe is so rotated that the measured portion is along the previously registered orientation ($\theta_0$), the position ($X_0$, $Y_0$) of the measured portion already determined in the step (A) remains unchanged.

The orientation of measurement indicates the angle formed by a beam for the measuring of the physical quantity and the normal direction of the measured portion. One of the orientations of measurement, which can be determined in various ways, is so determined that the orientation angle is zero. The orientation at the zero orientation angle, referred to as a reference orientation, can be sensed through the characteristics of the shape of the measured object for the measuring of the physical quantity in the reference orientation. When the measured object has a rectangular sectional shape in a Y-Z plane, for example, the energy of transmitted light is maximized at the zero orientation angle as shown in FIG. 3A. If the measured object has a circular sectional shape in the Y-Z plane, for example, the energy of the transmitted light is minimized at the zero orientation angle as shown in FIG. 3B. The sectional shape of the measured object in the Z-Y plane is not restricted to a rectangular or circular one but the reference orientation can be sensed through the characteristics of the distribution waveform of transmission energy also when the measured object has still another sectional shape. The physical quantity may be measured not in the reference orientation but in another orientation, which can be sensed from the waveform of the transmission energy. Furthermore, the orientation can be determined not through the waveform of the transmission energy itself but through the primary, secondary or higher order differential waveform thereof.

In order to implement this measuring method, a measuring apparatus according to an aspect of the present invention comprises a ring-shaped probe 2 which is set around a space where a measured portion 9 is arranged in a non-contact manner, sensors including positioning means 4, distance measuring means 6, orientation determination means 8 and a physical quantity measuring apparatus 10 which are arranged along the ring of the probe 2 and inwardly mounted thereon, a support mechanism (not shown) for the probe 2, a position control part (not shown), and a data processor (not shown), as shown in FIG. 2.

Assuming that a surface perpendicularly intersecting with the plane of the ring through the center of the probe 2 is an X-Y plane and an axis perpendicularly intersecting with the X-Y plane through the center of the probe 2 is a Z-axis, the support mechanism for the probe 2 supports the probe 2 to be movable in the X-, Y- and Z-axis directions and rotatable in the plane including the ring.

The position control part stores the position of an image indicating the measured portion 9, the distance between the measured portion 9 and a sensing position located on the intersection point between the ring and the Z-axis in measurement, and the orientation of the physical quantity measuring apparatus 10 with respect to the measured portion 9 in measurement for arranging the positioning means 4 on the sensing position with respect to the measured portion 9, which is arranged in a prescribed space in a non-contact state, and adjusting the position of the probe 2 by controlling the support mechanism in the X- and Y-axis directions when the positioning means 4 senses the previously registered image of the measured portion 9, so that the position of the sensed image coincides with that of the registered image, arranging the distance measuring means 6 on the sensing position, adjusting the position of the probe 2 by controlling the support mechanism in the Z-axis direction so that the distance up to the measured portion 9 sensed by the distance measuring means 6 is equal to the previously registered distance, arranging the orientation determination means 8 on the sensing position, determining such a position that the orientation of the measured portion 9 sensed by the orientation determination means 8 is equal to the previously registered orientation, arranging the physical quantity measuring apparatus 10 on the sensing position and moving the same to the position determined by the orientation determination means 8.

The data processor calculates the physical quantity from a sensing signal of the physical quantity measuring apparatus 10 positioned by the position control part.

In the measuring method shown in FIG. 1, the steps (A) to (D) may be repeated in every physical quantity measurement, for measuring the physical quantity a plurality of times. The measured object, which is brought into a non-contact state, cannot be fixed over a long time. Therefore, the physical quantity can be measured regularly under constant measuring conditions by adjusting the relative positions and the orientations of the measured portion and the physical quantity measuring apparatus in every physical quantity measurement Furthermore, the physical quantity can be measured under constant measuring conditions even if the measured object is in a moving state.

In order to facilitate the determination of the measuring conditions, it is preferable to employ a preliminary positioning apparatus to arrange the measured portion 9 in the prescribed space so that the preliminary positioning apparatus is removed after positioning and the measured portion 9 is arranged in a spatially non-contact manner, as shown in the upper portion of FIG. 1. Thereafter, the sensing position of the probe 2, the measured area (distance) and the measuring orientation are determined with respect to the measured portion 9 and thereafter the physical quantity measuring apparatus 10 is arranged on the sensing position of the probe 2 for the measuring of the physical quantity, as described above.

An example of the positioning means 4 is a two-dimensional image sensor such as a CCD camera.

An example of the distance measuring means 6 comprises a first light beam application optical system for irradiating the measured object with a light beam, a position sensitive device for receiving the light beam reflected by the measured object and a photoreceptor optical system for condensing the light reflected by the measured object on the position sensitive device, for sensing the distance between the sensing position and the measured object through the condensed position on the position sensitive device.

An example of the orientation determination means 3 includes a second light beam application optical system for irradiating the measured object with a light beam while changing the orientation, and a photoreceptor part for sensing the light beam transmitted through the measured object, to determine an incident angle of measuring light for the measuring of the physical quantity through the intensity of the transmitted light sensed by the photoreceptor part or a differential value thereof.

The first and second light beam application optical systems can comprise laser units as light sources.

The position control part preferably comprises a program for executing a function of positioning the probe. Thus, operations from positioning to physical quantity measurement can be automatically executed when the measured object is arranged on a prescribed position.

Furthermore, the position control part preferably repeats the program for positioning the probe in every physical quantity measurement when measuring the physical quantity a plurality of times. Thus, the physical quantity measurement can be automatically executed regularly under constant measuring conditions.

According to the present invention, the physical quantity is measured after arranging the measured object in the space and determining the position of the probe, the distance and the orientation in response to the measured object, whereby non-invasive measurement can be performed in a non-contact state in excellent repeatability.

Due to the non-contact measurement, the measured object is neither physically nor mentally influenced by the probe, dispersion of measured data can be suppressed, and the measurement can be performed in excellent reproducibility.

The foregoing along with other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
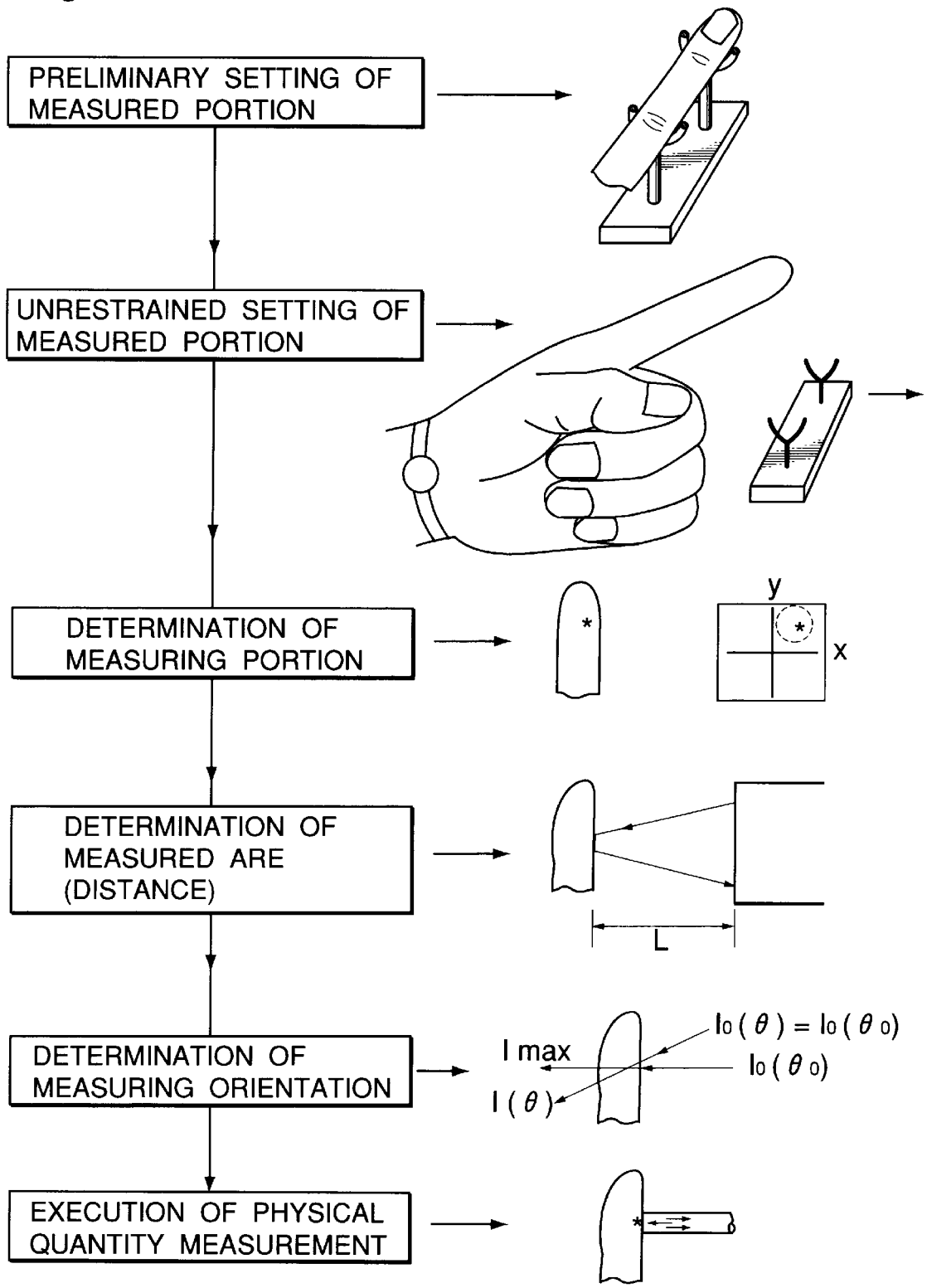
FIG. 1 is a schematic flow chart showing a method according to the present invention.
Figure 2:
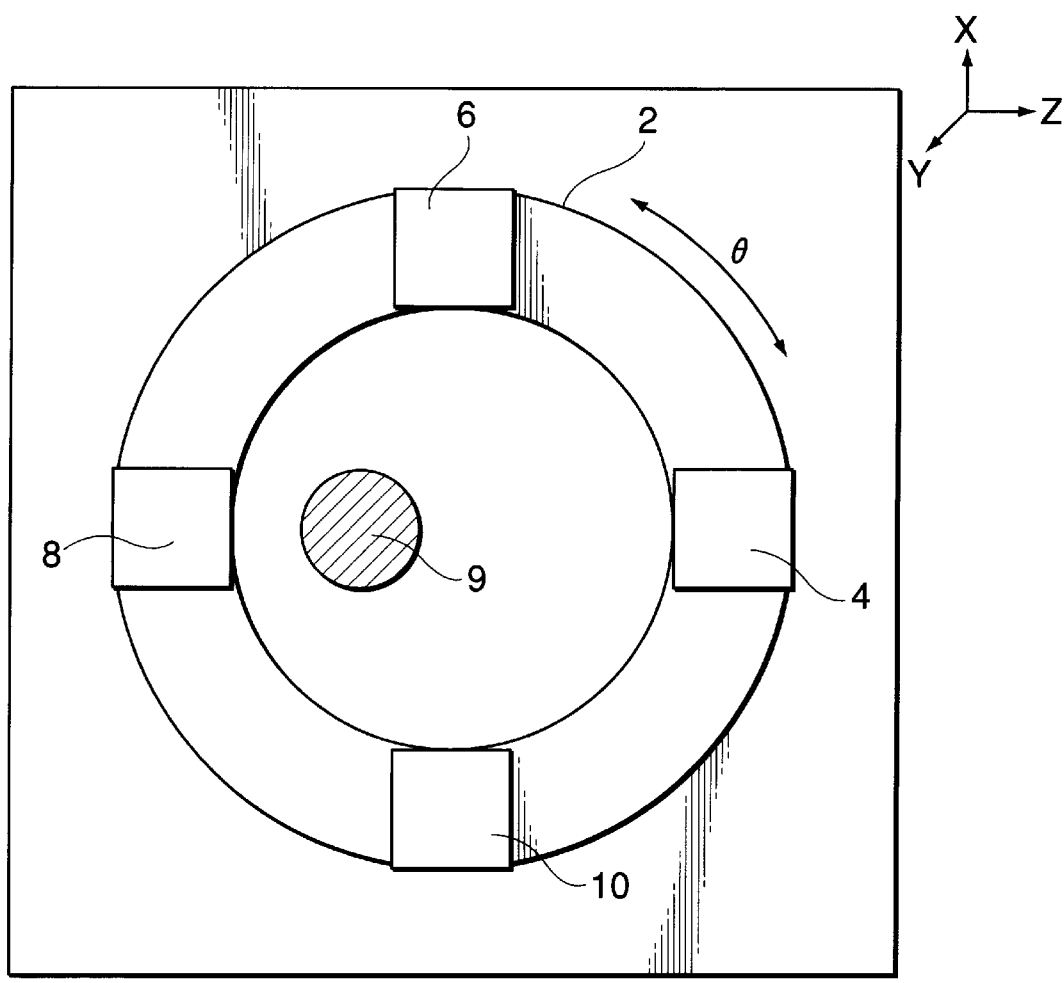
FIG. 2 is a schematic block diagram showing an apparatus according to the present invention.
Figure 3A:
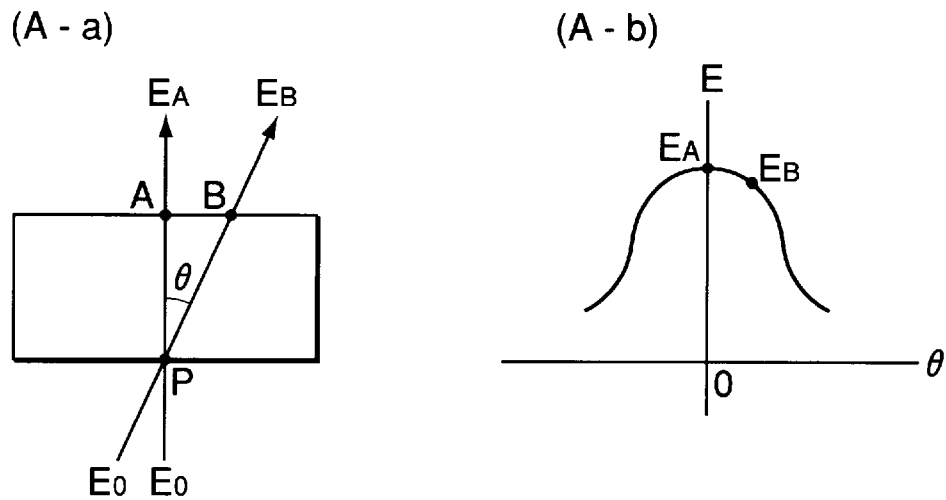
FIGS. 3A and 3B illustrate the relation between optical paths of transmitted light and measuring orientation angles θ and the relation between the measuring orientation angles θ and the quantities of the transmitted light respectively for the showing of the principle of determination of the measuring orientation.
Figure 3B:
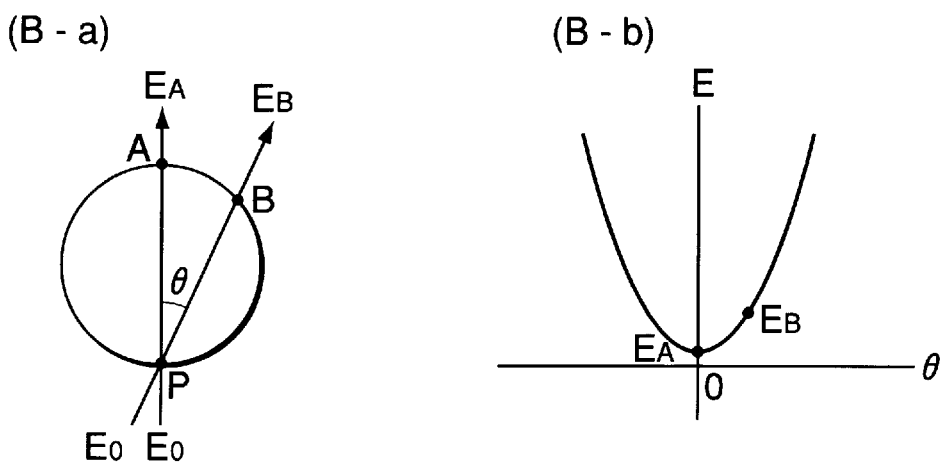
Figure 4:
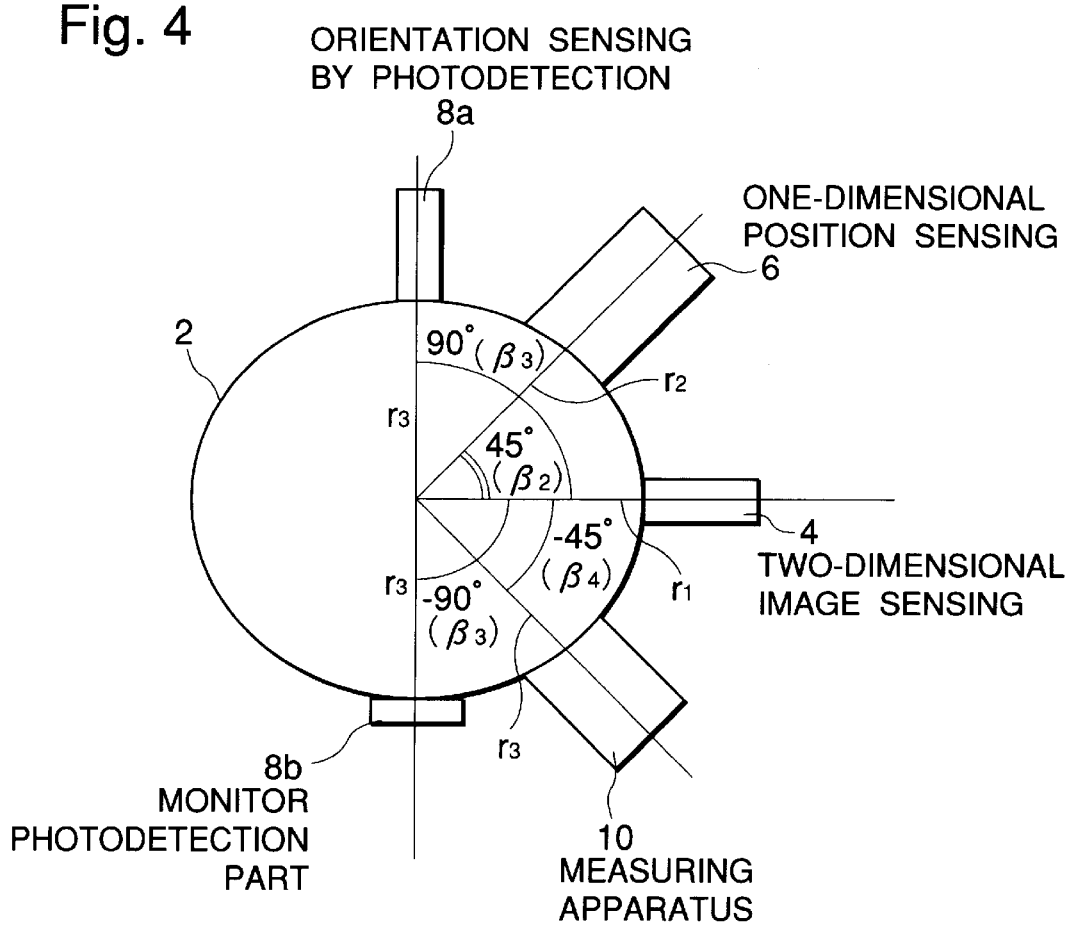
FIG. 4 is a schematic plan view showing the arrangement of two-dimensional image sensing means, distance measuring means, orientation determination means and a physical quantity measuring apparatus with respect to a probe.

FIG. 4 shows the arrangement of two-dimensional image sensing means 4, distance measuring means 6, orientation determination means 8 and a physical quantity measuring apparatus 10 with respect to a probe 2. The orientation determination means 8 consists of a beam application part 8a and a photoreceptor part 8b, which are arranged on both diametral ends of a ring forming the probe 2. The two-dimensional image sensing means 4 for positioning is arranged in a direction perpendicular to that of arrangement of the beam application part 8a and the photoreceptor part 8b, and the distance measuring means 6 and the physical quantity measuring apparatus 10 are arranged on positive and negative positions of 45° with reference to the position of the two-dimensional image sensing means 4 respectively.

Figure 5:
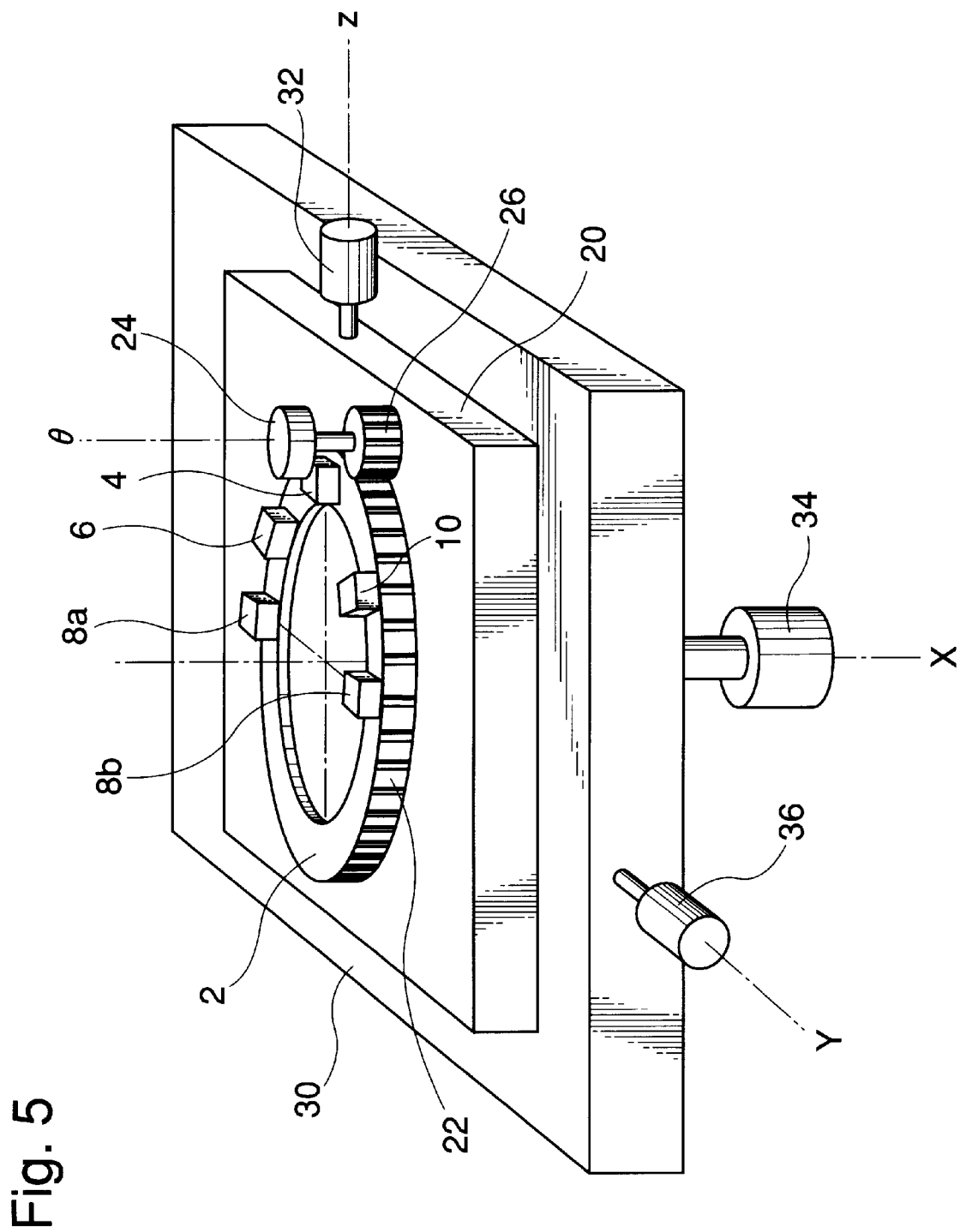
FIG. 5 is a perspective view showing a measuring apparatus according to an embodiment of the present invention.

FIG. 5 shows a measuring apparatus according to an embodiment of the present invention. A probe 2 is rotatably supported on a Z stage 20, and a gear 22 is provided on a side surface of the probe 2 to fit with another gear 26 mounted on a rotary shaft of a motor 24. Thus, the probe 2 rotates following rotation of the motor 24. The rotation of the probe 2 arranges two-dimensional image sensing means 4, distance measuring means 6, a beam application part 8a, a photoreceptor part 8b and a physical quantity measuring apparatus 10 on a sensing position while adjusting an orientation angle. The probe 2 rotates at an angle θ.

The Z stage 20 is mounted on an X-Y stage 30, to be movable in a Z-axis direction following rotation of a motor 32.

The X-Y stage 30 is supported by a supporter (not shown), to be movable in X- and Y-axis directions following rotation of X and Y motors 34 and 36 respectively.

A position control part (not shown) controls the movement of the stages 20 and 30 following rotation of the motors 32, 34, 36 and 24 and the rotation of the probe 2 under previously set conditions.

Figure 6:
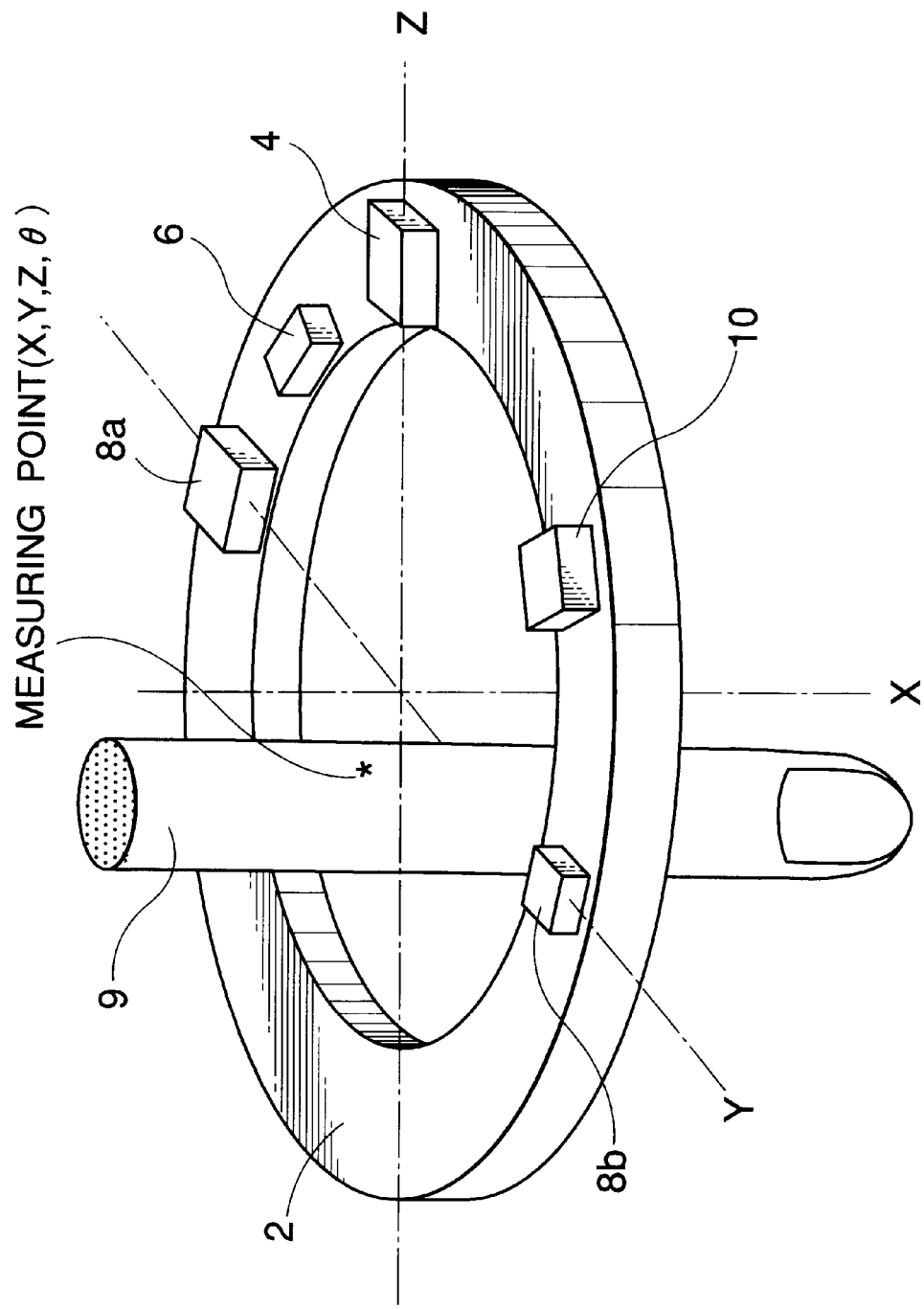
FIG. 6 is a perspective view showing the relative positional relation between a probe, various sensors and a measured object.

FIG. 6 shows the relative positional relation between the probe 2, the various sensors 4, 6, 8a, 8b and 10 and a measured object (e.g., a finger) 9. The Z-axis and the ring forming the probe 2 intersect with each other on the sensing position where the two-dimensional image sensing means 4 is arranged in FIG. 6. The two-dimensional image sensing means 4, the distance measuring means 6, and the beam application part 8a are arranged on the sensing position respectively for adjusting the position of the probe 2 and determining the orientation thereof, and thereafter the physical quantity measuring apparatus 10 is arranged on the sensing position for measuring the physical quantity.

Figure 7:
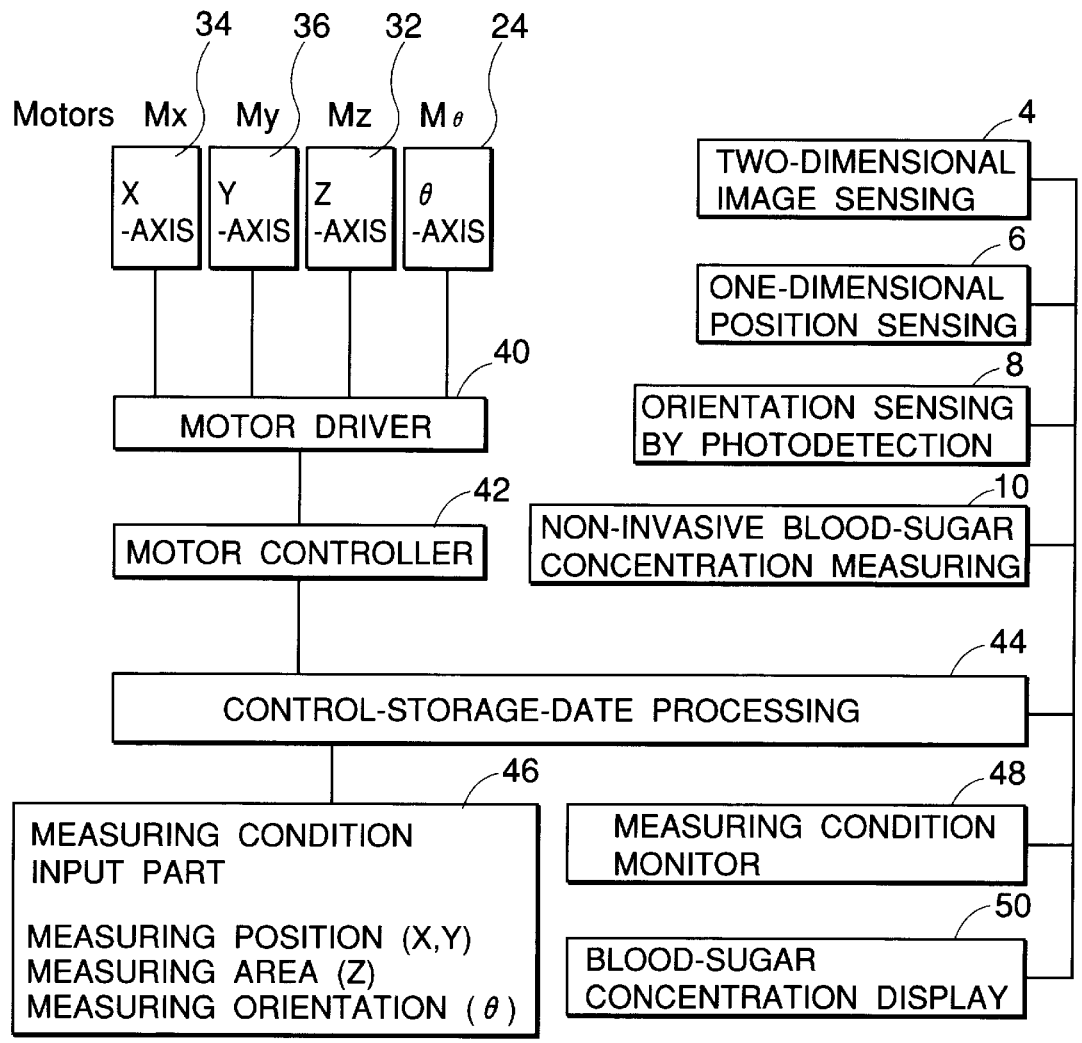
FIG. 7 is a block diagram schematically showing the overall apparatus according to the embodiment of the present invention.

FIG. 7 schematically illustrates the overall apparatus according to the embodiment. A motor driver circuit 40 is provided for driving the motors 24, 32, 34 and 36, and a control•storage•data processing unit 44 serving both as a position control part and a data processor controls a motor controller 42 controlling operations of the motor driver circuit 40. A two-dimensional image sensor 4 serving as positioning means, a one-dimensional position sensor 6 serving as distance measuring means and an orientation sensor 8 serving as orientation determination means are provided on the probe 2 as sensors. The two-dimensional image sensor 4, the one-dimensional position sensor 6 and the orientation sensor 8 are adapted to determine the sensing position (X, Y), the measured distance Z, i.e., the measured area, and the measuring orientation θ respectively. The control•storage•data processing unit 44 controls operations of these sensors, and further controls the motors 24, 32, 34 and 36 through the motor controller 42 to attain the previously set conditions on the basis of sensing signals from the sensors. The control•storage•data processing unit 44 data-processes a sensing signal from a non-invasive blood-sugar concentration measuring apparatus 10 serving as a physical quantity measuring apparatus, and a display 50 displays the same. The display 50 which is a part displaying a result of measurement of the physical quantity displays blood-sugar concentration. An input part 46 inputs the measuring conditions of the sensing position (X, Y), the measured area (distance) Z and the measuring orientation θ in the control-storage-data processing unit 44, and a measuring condition monitor unit 48 monitors and displays the state of the probe 2.

Figure 8:
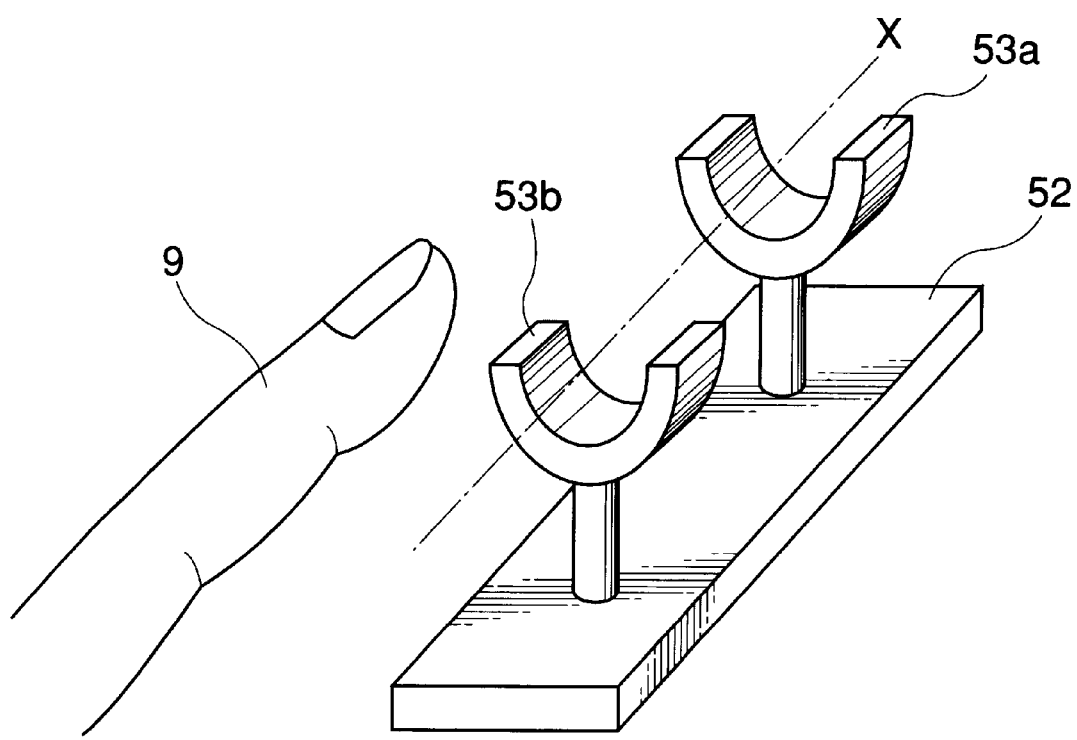
FIG. 8 is a perspective view showing a temporary direction determining apparatus for preliminarily determining the position and the orientation of a measured object which is arranged in a space.

Apparatuses for determining the measuring conditions in this embodiment are described as followed:

FIG. 8 shows a stand 52 serving as a temporary direction determining apparatus for preliminarily determining the position and the direction for arranging the measured object 9, which is a finger, in a space. The stand 52 is adapted to receive the finger 9 thereon for positioning the same along the X-axis, and comprises two U-shaped support parts 53a and 53b supporting the finger 9. The stand 52 may alternatively be formed by a simple pipe, or may comprise a single saddlelike support part.

The stand 52 is a preliminary element, which is set to be removed after determining the arrangement of the finger 9. In consideration of stability of position settings, the measured object 9 may alternatively be roughly positioned while leaving a partial support coming into contact with the measured object 9 on a position not much exerting physical influence thereon.

Figure 9A:
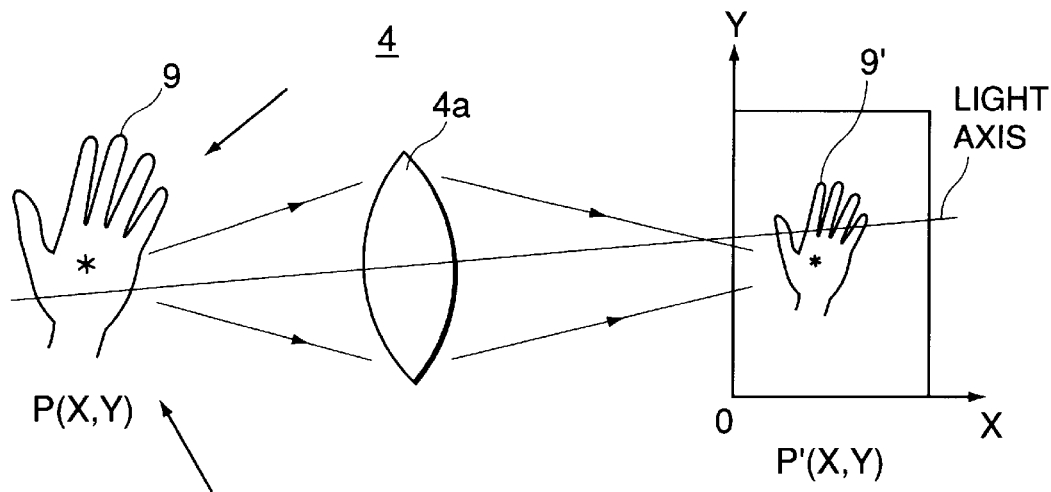
FIG. 9A schematically illustrates the two-dimensional image sensing means for determining a sensing position.

FIG. 9A schematically shows the two-dimensional image sensing means 4 for settling the sensing position. In order to position the measured object 9, the probe 2 is moved in the X-Y plane for locating a previously registered measuring portion such as an asterisk provided on a finger, for example, on a registered position $(X_0, Y_0)$. The two-dimensional image sensing means 4 is formed by an image reader comprising a two-dimensional CCD camera, for example, and additionally including an illuminator and a display as a set.

Figure 9B:
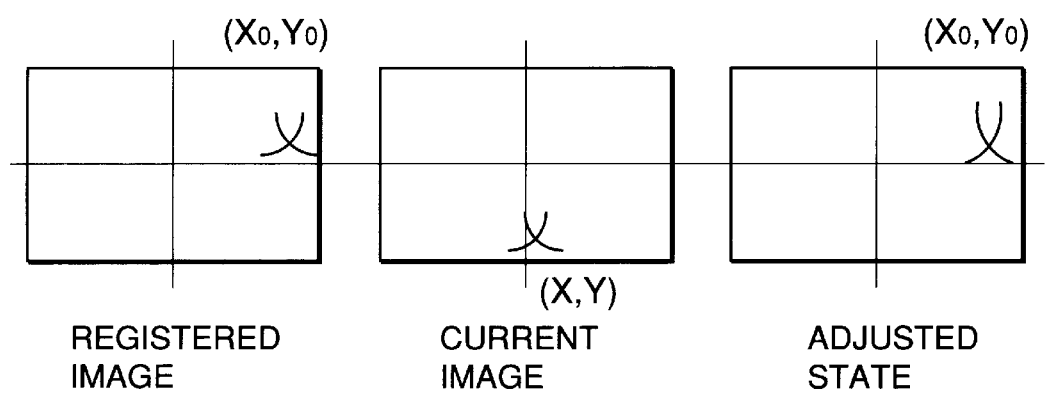
FIG. 9B illustrates a process of positioning.

FIG. 9B shows the process of positioning. Assuming that a current read image is expressed as (X, Y) with respect to the position $(X_0, Y_0)$ of the registered image, the probe 2 is adjusted in the X- and Y-axis directions so that the position of an incorporated image coincides with that of the registered image.

Figure 10A:
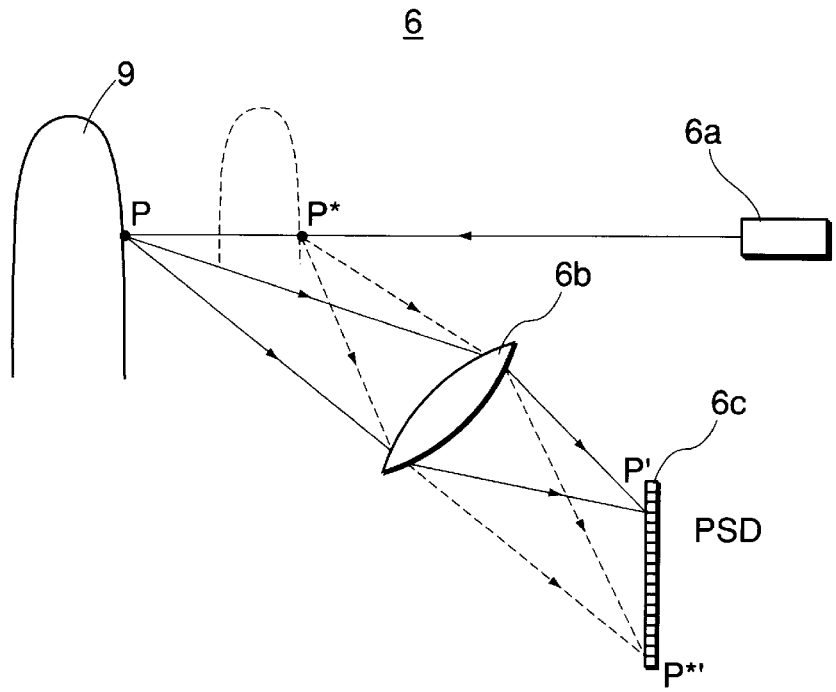
FIG. 10A schematically illustrates the distance measuring means for the settling of a measured area.

FIG. 10A shows exemplary distance measuring means 6 for adjusting the measured area to the registered one. The distance measuring means 6 sets the measured area by adjusting the distance between the measured object 9 and the measuring apparatus to the previously registered one. After adjusted in the X- and Y-axis directions, therefore, the probe 2 is rotated to arrange the distance measuring means 6 on the sensing position. The distance measuring means 6 comprises a laser unit 6a for irradiating the measured object 9 with a laser beam, a PSD (position sensitive device) 6c for receiving the laser beam reflected by the measured object 9 and a lens 6b for condensing the light reflected by the measured object 9 on the PSD 6c. An image forming position on the PSD 6c corresponds to and varies with the distance between the laser unit 6a and the measured object 9, and hence the probe 2 is moved in the Z-axis direction for locating the image forming position on the PSD 6c on the previously registered position.

Figure 10B:
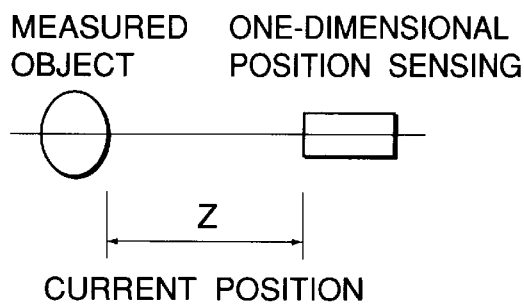
FIGS. 10B and 10C illustrate distance adjusting processes thereof.
Figure 10C:
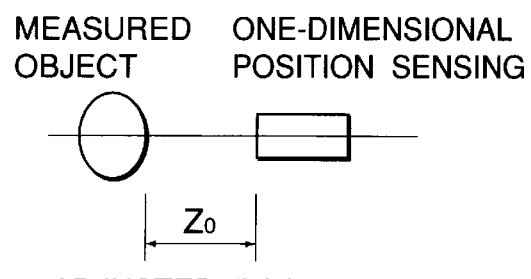

FIGS. 10B and 10C illustrate processes of adjusting the probe 2 in the Z-axis direction so that a current position Z is equal to a registered position $Z_0$.

When a position P(X, Y, Z) is adjusted to be $P(X_0, Y_0, Z_0)$, it comes to that the measured position is located on a rotation center of the orientation angle θ, i.e., on the X-axis.

After the measured area is determined, the measuring orientation, which is an incident angle of light, is also determined. In order to determine the measuring orientation, the intensity of transmitted light from the measured object 9 is detected. When light is transmitted through the measured object 9, the intensity of the transmitted light is reduced as the thickness of the measured object 9 is increased. Therefore, a path length corresponding to an incident angle maximizing the intensity of the transmitted light is the shortest The incident angle of light corresponding to the shortest path length is employed as an incidence orientation for measuring the physical quantity.

Figure 11A:
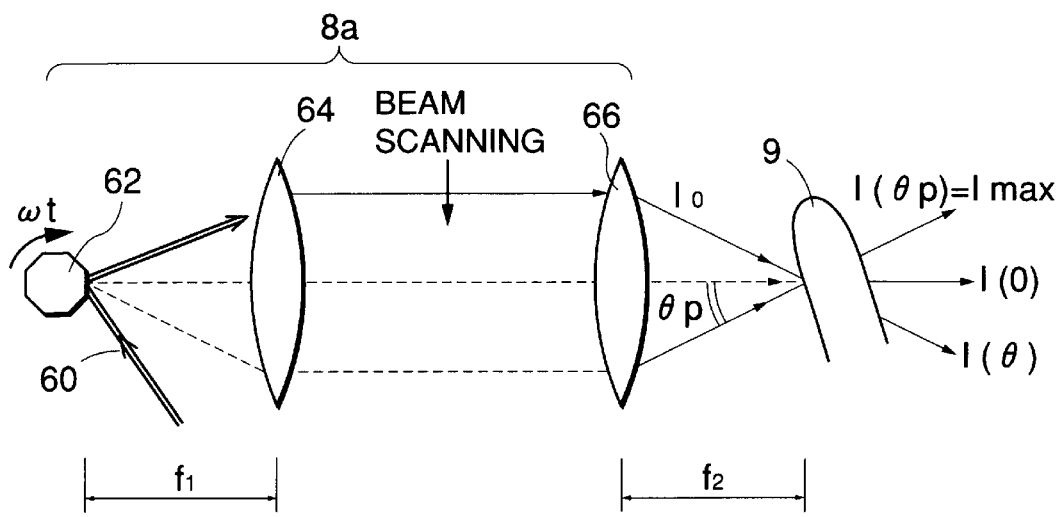
FIG. 11A schematically illustrates the orientation determination means.
Figure 11B:
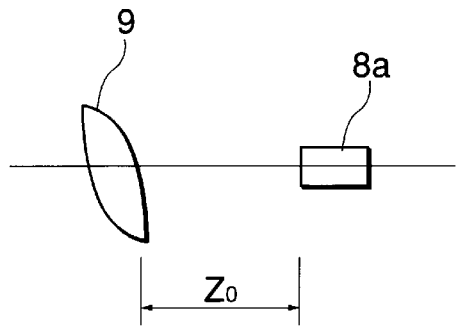
FIGS. 11B and 11C illustrate a process of orientation determination.
Figure 11C:
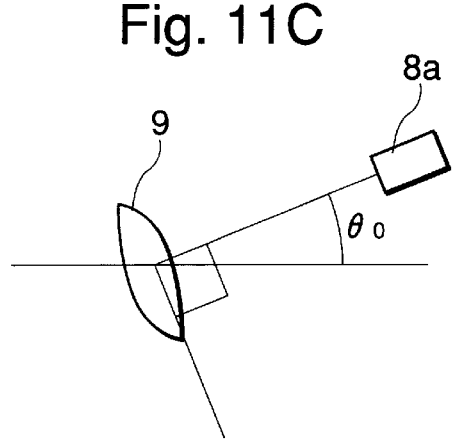

FIG. 11A shows exemplary orientation determination means 8, which includes a beam application part 8a and a photoreceptor part The beam application part 8a introduces a laser beam 60 into a polygon mirror 62, and further introduces light reflected by the polygon mirror 62 into a lens 64. When the polygon mirror 62 is so arranged that the reflecting surface thereof is on the focal position of the lens 64, the light reflected by the polygon mirror 62 passes through the lens 64 and forms a beam parallel to the optical axis of an optical system of the lens 64. A lens 66 condenses the parallel beam and introduces the same into the measured object 9, so that the photoreceptor part senses the light transmitted through the measured object 9. The lens 66 is so arranged that the measured object 9 is on the focal position thereof, whereby the laser beam 60 passing through the lens 66 enters the same position of the measured object 9. The photoreceptor part senses the light transmitted through the measured object 9 for regarding an incident angle θp maximizing the intensity of the transmitted light as an incident angle (measuring orientation) $θ_0$ of the measuring light for measuring the physical quantity. FIGS. 11B and 11C show processes of adjusting the measuring orientation $θ_0$.

Figure 12:
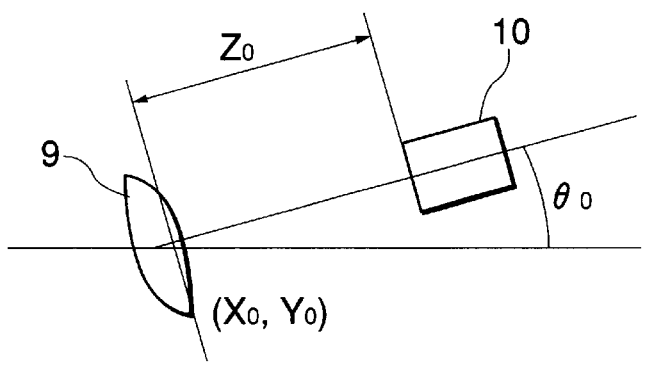
FIG. 12 schematically illustrates a state of arranging the physical quantity measuring apparatus on a determined position of the probe for making measurement.

After measuring the position $(X_0, Y_0)$, the measured area (distance) $(Z_0)$ and the measuring orientation $(θ_0)$ in the aforementioned manner, the physical quantity measuring apparatus 10 for measuring a blood-sugar level or the like as the physical quantity is arranged on the determined position of the probe 2 as shown in FIG. 12, for measuring the physical quantity under the determined conditions.

Figure 13:
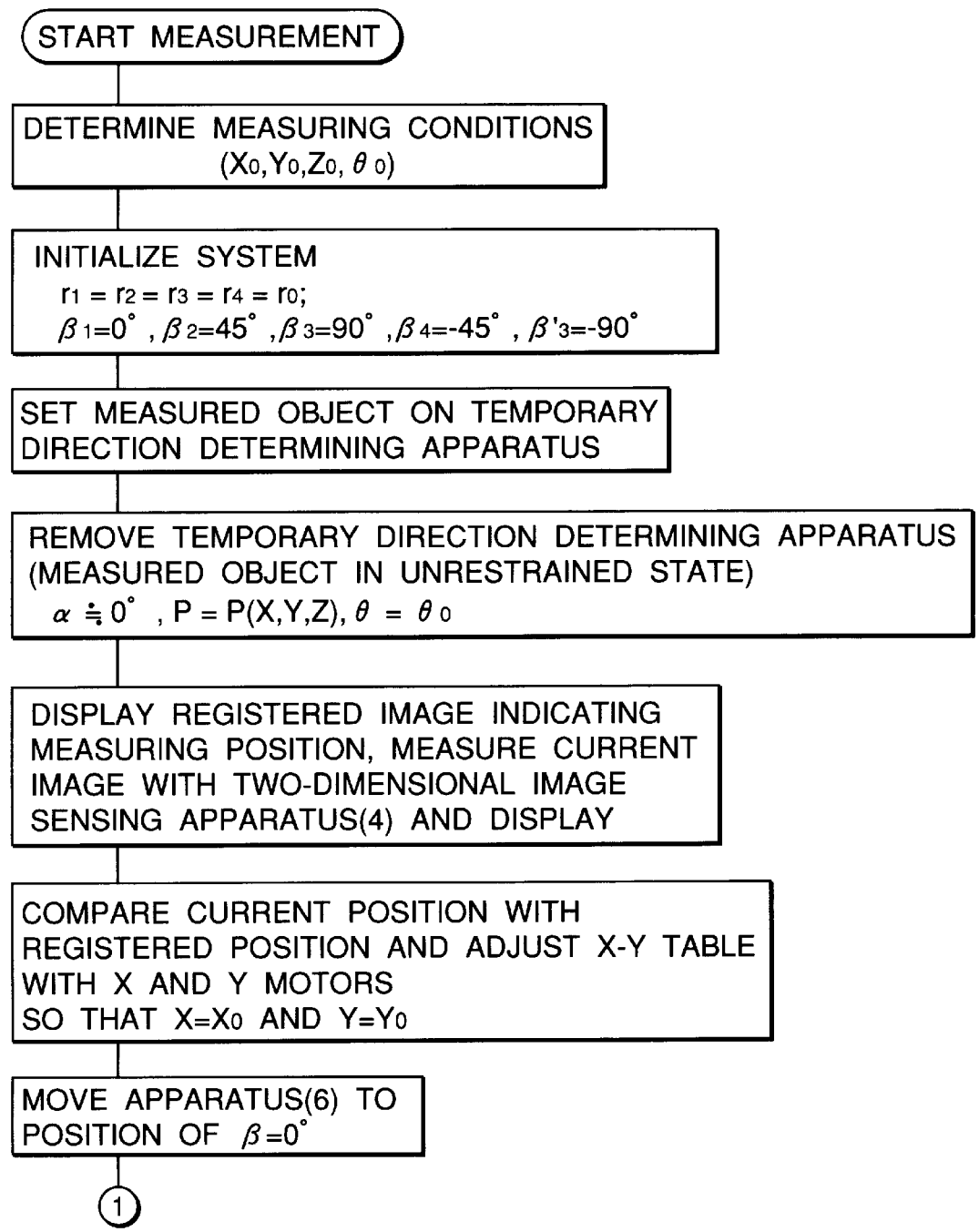
FIG. 13 is a flow chart showing a front half part of operations, from the determination of measuring conditions up to physical quantity measurement.
Figure 14:
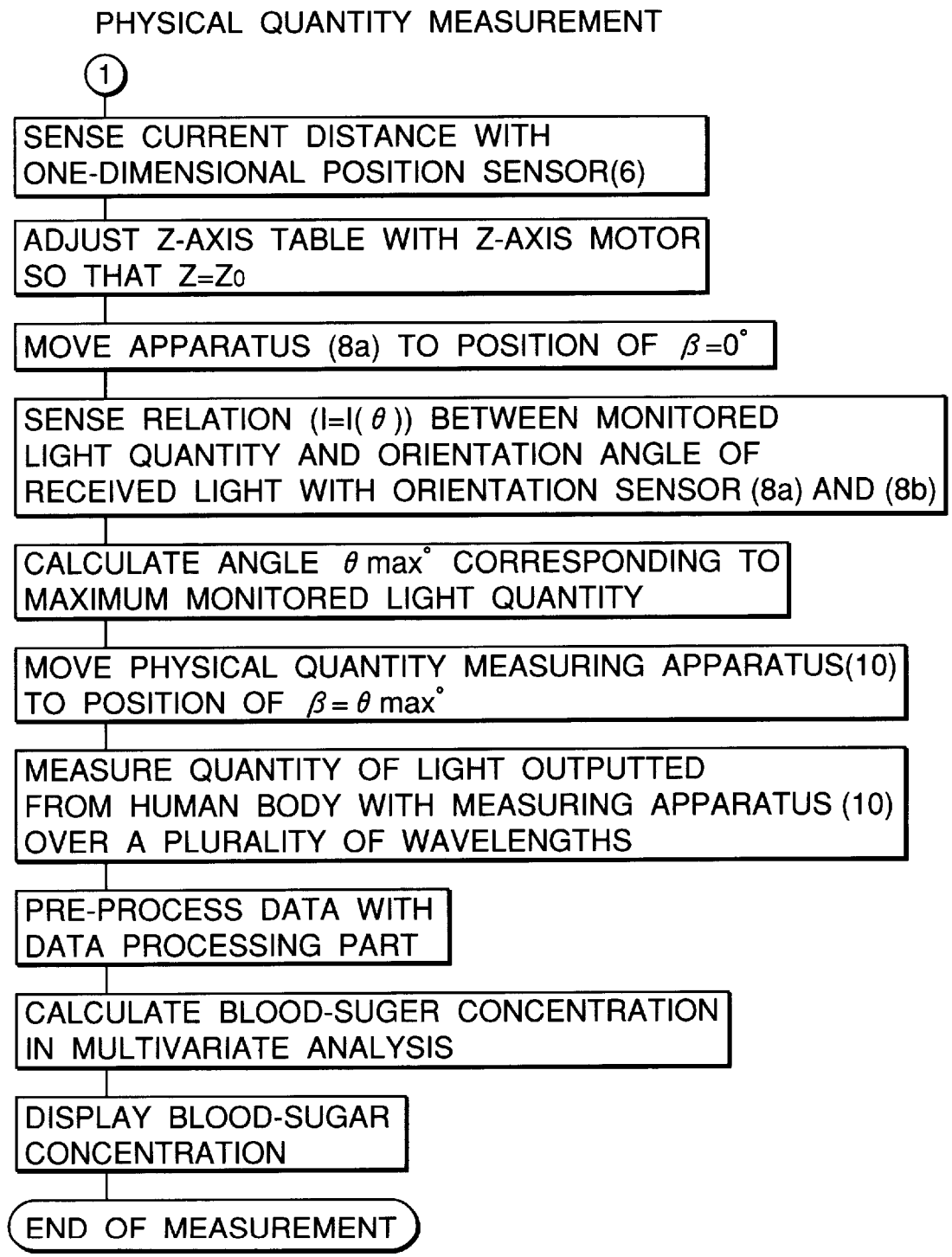
FIG. 14 is a flow chart showing a rear half part of operations, from the determination of measuring conditions up to physical quantity measurement.

FIGS. 13 and 14 are flow charts of operations, from the determination of the measuring conditions up to measurements of the physical quantity (e.g., a blood-sugar level). When the measurement is started, the measuring conditions $(X_0, Y_0, Z_0$ and $θ_0)$ are first determined. If the measurement is an initial one, the two-dimensional image sensing means 4 incorporates a characteristic image and newly registers the coordinates $(X_0, Y_0)$ of a characteristic point. On the other hand, if the measurement is a second one, the registered coordinates $(X_0, Y_0)$ are called and referred to.

Thereafter the measuring apparatus is initialized. In this embodiment, the probe 2 is initialized as shown in FIG. 4.

Thereafter the temporary direction determining apparatus shown in FIG. 8 sets the measured object 9 on a prescribed position. In this state, the angle α between a set axis of the measured object 9 and the X-axis is 0°, and the orientation angle θ is at the measured angle $θ_0$. The position P(X, Y, Z) is not yet on the position $(X_0, Y_0, Z_0)$ for measurement The temporary direction determining apparatus is removed and the measured object 9 is arranged in the space in a non-contact state.

First, the probe 2 is rotated to move the two-dimensional image sensing means 4 on the sensing position so that the two-dimensional image sensing means 4 incorporates the current image and displays the same on the monitor 48.

The current position incorporated by the two-dimensional image sensing means 4 is compared with the registered position and the X and Y motors 34 and 36 are so controlled that the current position (X, Y) reaches the registered position $(X_0, Y_0)$.

Second, the probe 2 is rotated to bring the distance measuring means 6 of the one-dimensional position sensor into the sensing position so that the distance measuring means 6 detects the current distance and a Z motor is so driven that $Z=Z_0$.

Then, the probe 2 is rotated to bring the beam application part 8a of the orientation determination means 8 into the sensing position, so that the beam application part 8a irradiates the measured object 9 with the laser beam while changing the orientation, and the photoreceptor part 8b senses the transmitted light for determining an orientation angle θmax maximizing the quantity of the transmitted light.

Thereafter the probe 2 is so rotated that the physical quantity measuring apparatus 10 is at the orientation angle θmax determined in the above from the sensing position. At this position, the measured object 9 is irradiated with measuring light over a plurality of wavelengths and a data processor senses and data-processes output light The data processor calculates a blood-sugar level by multivariate analysis, for example, and the display 50 displays the value.

Figure 15:
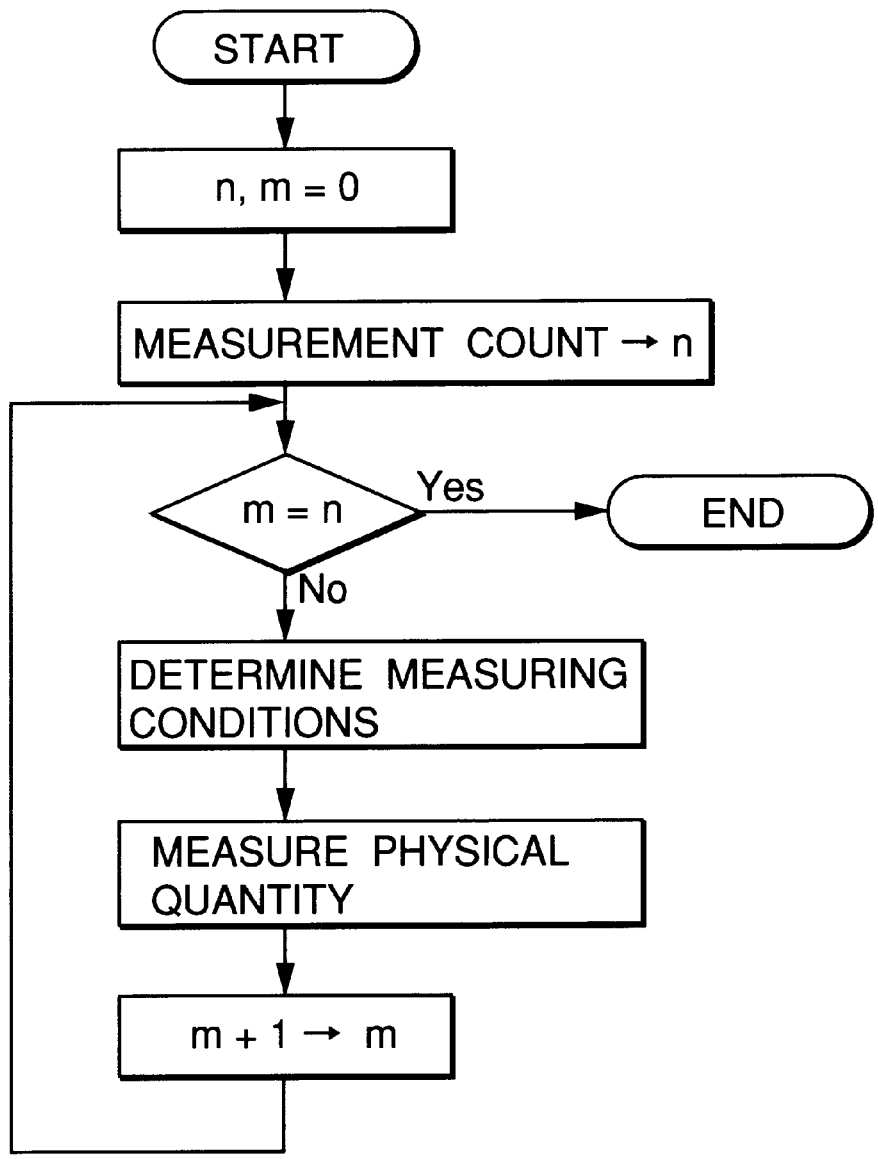
FIG. 15 is a flow chart showing a procedure in case of repetitively performing measurements a plurality of times.

FIG. 15 shows a procedure of repeatedly measuring the physical quantity a plurality of times. A measurement count "m" is initialized at zero, and a measurement count "n" is set The position $(X_0, Y_0)$, the distance $Z_0$ and the orientation $θ_0$ are determined as the measuring conditions as shown in FIGS. 13 and 14 for the measuring of the physical quantity, and "1" is added to the measurement count "m". This operation is repeated until the measurement count "m" is equal to the measurement count "n".

While the measuring conditions are determined every measurement in FIG. 15, the physical quantity may be continuously measured "n" times after determining the measuring conditions once if it is conceivable that the measured object is substantially unmoved when the probe is adjusted.

Although the present invention has been described and illustrated in detail, it is clearly understood that the same is by way of illustration and example only and is not to be taken by way of limitation, as the spirit and scope of the present invention is limited only by the terms of the appended claims.

We claim:

1. A non-contact non-invasive measuring method for measurements by previously registering an image indicating a measured portion, the distance between said measured portion and a physical quantity measuring apparatus, and the orientation of said physical quantity measuring apparatus with respect to said measured portion in measurement, and determining the position and the orientation of said physical quantity measuring apparatus through steps of:

(A) arranging a measured object in a prescribed space in a non-contact state while arranging positioning means on a sensing position of a probe for sensing said previously registered image of said measured portion with said positioning means and adjusting the position of said probe so that the position of sensed said image coincides with that of said registered image;

(B) arranging distance measuring means on said sensing position of said probe and adjusting the position of said probe so that the distance up to said measured portion reaches said previously registered distance;

(C) arranging orientation determination means on said sensing position of said probe and determining such a sensing position that said measured portion is in said previously registered orientation; and (D) thereafter arranging said physical quantity measuring apparatus on said sensing position of said probe, moving the same to said position determined by said orientation determination means, thereafter irradiating said measured portion with measuring light from said physical quantity measuring apparatus and sensing output light from said measured portion thereby obtaining a physical quantity.

2. The non-contact non-invasive measuring method in accordance with claim 1, wherein said probe is in the form of a ring so that said measured portion is arranged at the center of said probe, and said previously registered distance up to said measured portion in said step (B) is set equal to the radius of said ring forming said probe.

3. The non-contact non-invasive measuring method in accordance with claim 1, wherein said step (A) includes a step of positioning said measured object with a preliminary positioning apparatus and thereafter removing said preliminary positioning apparatus thereby arranging said measured object in said prescribed space in a non-contact state.

4. The non-contact non-invasive measuring method in accordance with claim 1, repeating an operation of determining the position and the orientation of said physical quantity measuring apparatus for measuring said physical quantity a plurality of times.

5. A measuring apparatus comprising.

a probe in the form of a ring being set around a space where a measured portion is arranged in a non-contact state;

a support mechanism supporting said probe to be movable in X-, Y- and Z-axis directions assuming that a single plane perpendicularly intersecting with the plane of said ring through the center of said probe is an X-Y plane and an axis perpendicularly intersecting with said X-Y plane through the center of said probe is a Z-axis while rotatably supporting said probe in a plane including said ring;

sensors including positioning means, distance measuring means, orientation determination means and a physical quantity measuring apparatus being arranged along said ring of said probe and mounted inward;

a position control part storing the position of an image indicating said measured portion, the distance between said measured portion and a sensing position located on the intersection point between said ring and said Z-axis in measurement, and the orientation of said physical quantity measuring apparatus with respect to said measured portion in measurement for arranging said positioning means on said sensing position with respect to a measured object being arranged in a prescribed space in a non-contact state, and adjusting the position of said probe by controlling said support mechanism in said X- and Y-axis directions when said positioning means senses a previously registered image of said measured portion so that the position of said sensed image coincides with that of said registered image, arranging said distance measuring means on said sensing position, adjusting the position of said probe by controlling said support mechanism in said Z-axis direction so that said distance up to said measured portion sensed by said distance measuring means reaches a previously registered distance, arranging said orientation determination means on said sensing position, determining such a position that said measured portion sensed by said orientation determination means is in a previously registered orientation, arranging said physical quantity measuring apparatus on said sensing position and moving the same to said position determined by said orientation determination means; and a data processor calculating a physical quantity from a sensing signal of said physical quantity measuring apparatus positioned by said position control part.

6. The measuring apparatus in accordance with claim 5, wherein said positioning means is a two-dimensional image sensor.

7. The measuring apparatus in accordance with claim 5, wherein said distance measuring means comprises a first light beam irradiation optical system for irradiating said measured object with a light beam, a position sensing device receiving said light beam reflected by said measured object, and a photoreceptor optical system for condensing said light beam reflected by said measured object on said position sensitive device, for sensing the distance between said sensing position and said measured object on the basis of a condensing position on said position sensitive device.

8. The measuring apparatus in accordance with claim 5, wherein said orientation determination means is provided with a second light beam irradiation optical system for irradiating said measured object with a light beam while changing the orientation and a photoreceptor part, for sensing said light beam transmitted through said measured object, and determining an incident angle of measuring light for measuring said physical quantity by the intensity of transmitted light sensed by said photoreceptor part or a differential value thereof.

9. The measuring apparatus in accordance with claim 5, further comprising a detachable temporary direction determining apparatus for preliminarily determining the position and direction for arranging said measured object in said prescribed space.

10. The measuring apparatus in accordance with claim 5, wherein said position control part comprises a program for executing a function for positioning said probe.

11. The measuring apparatus in accordance with claim 5, wherein said position control part is adapted to repeat a program for positioning said probe in every physical quantity measurement for measuring said physical quantity a plurality of times.

* * * * *